United States Patent [19]

Bogatzki

[11] Patent Number: 4,760,731

[45] Date of Patent: Aug. 2, 1988

[54] METHOD AND APPARATUS FOR THE STRESS TESTING OF GLASS CONTAINERS ARRANGED HANGING

[75] Inventor: Hans-Ulrich Bogatzki, Zurich, Switzerland

[73] Assignee: Elpatronic AG, Switzerland

[21] Appl. No.: 57,489

[22] Filed: Jun. 3, 1987

[30] Foreign Application Priority Data

Jun. 3, 1986 [CH] Switzerland .................... 02247/86

[51] Int. Cl.⁴ ............................................. G01N 3/34
[52] U.S. Cl. .................................... 73/12; 73/809
[58] Field of Search .................. 73/12, 809, 810, 41, 73/819, 821, 824

[56] References Cited

U.S. PATENT DOCUMENTS 3,896,657  7/1975  Brandt et al. .......................... 73/12
3,955,408  5/1976  Northup ........................... 73/824 X Primary Examiner—Jerry W. Myracle Attorney, Agent, or Firm—McCormick, Paulding and Huber

[57] ABSTRACT

A method and an apparatus are described for the stress testing of glass containers (10) which are arranged hanging, by impulse action on the bottom (14) of the container through the adjustable action of force on an impacting rod (12) resting on the bottom (14) of the container. For the action of the force, an adjustable source of energy (26) is used which may comprise an eccentric, an ultrasonic transmitter (26b), a magnetic actuating drive or the like, which acts on the end (18) of the rod (12), resting on the bottom of the container, remote from the bottom (14) of the container. The shaking exerted on the glass container during subsequent filling can be simulated by the action of the force which is adjustable in duration and/or amplitude, so that glass containers suspected of breakage can be eliminated by the stress test before being filled. The action of force can be proportioned in a simple manner so that optimum test vibration values can easily be adjusted.

14 Claims, 3 Drawing Sheets

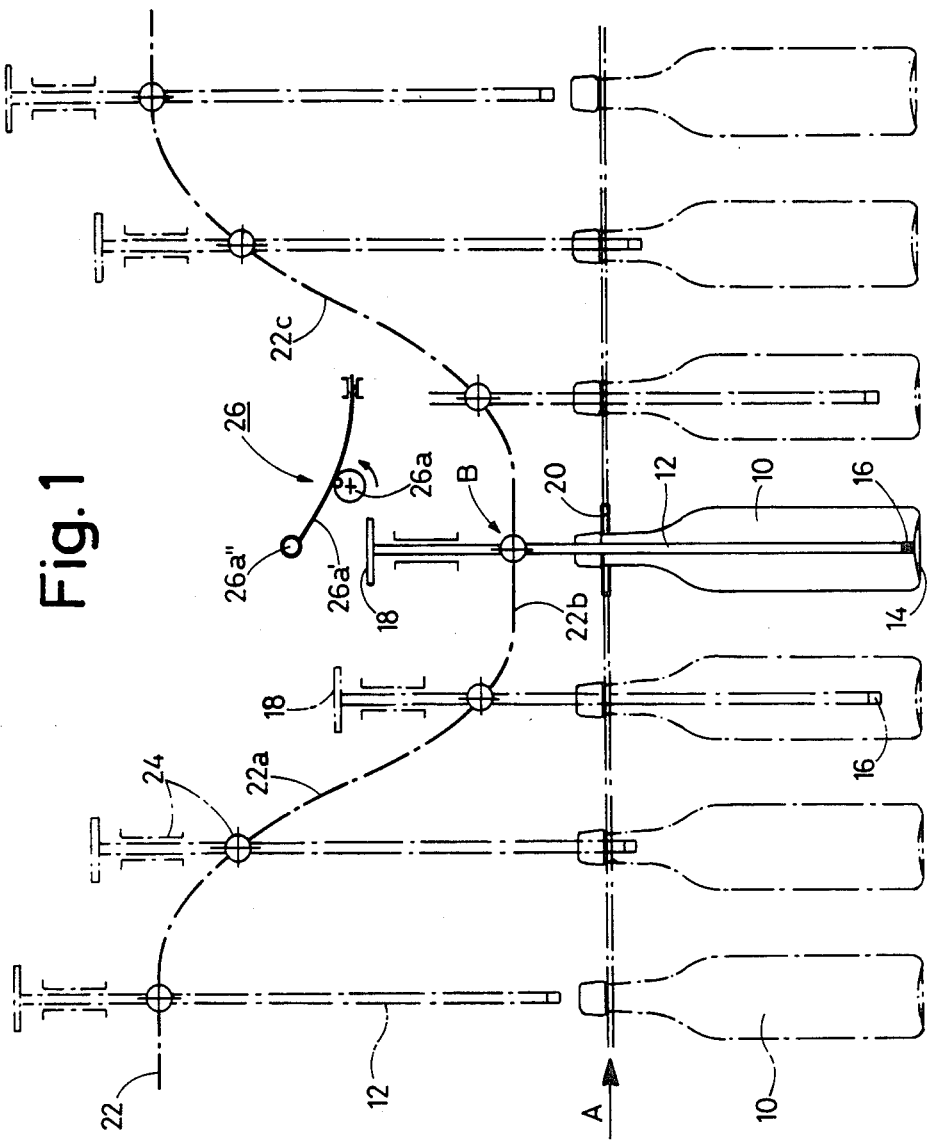

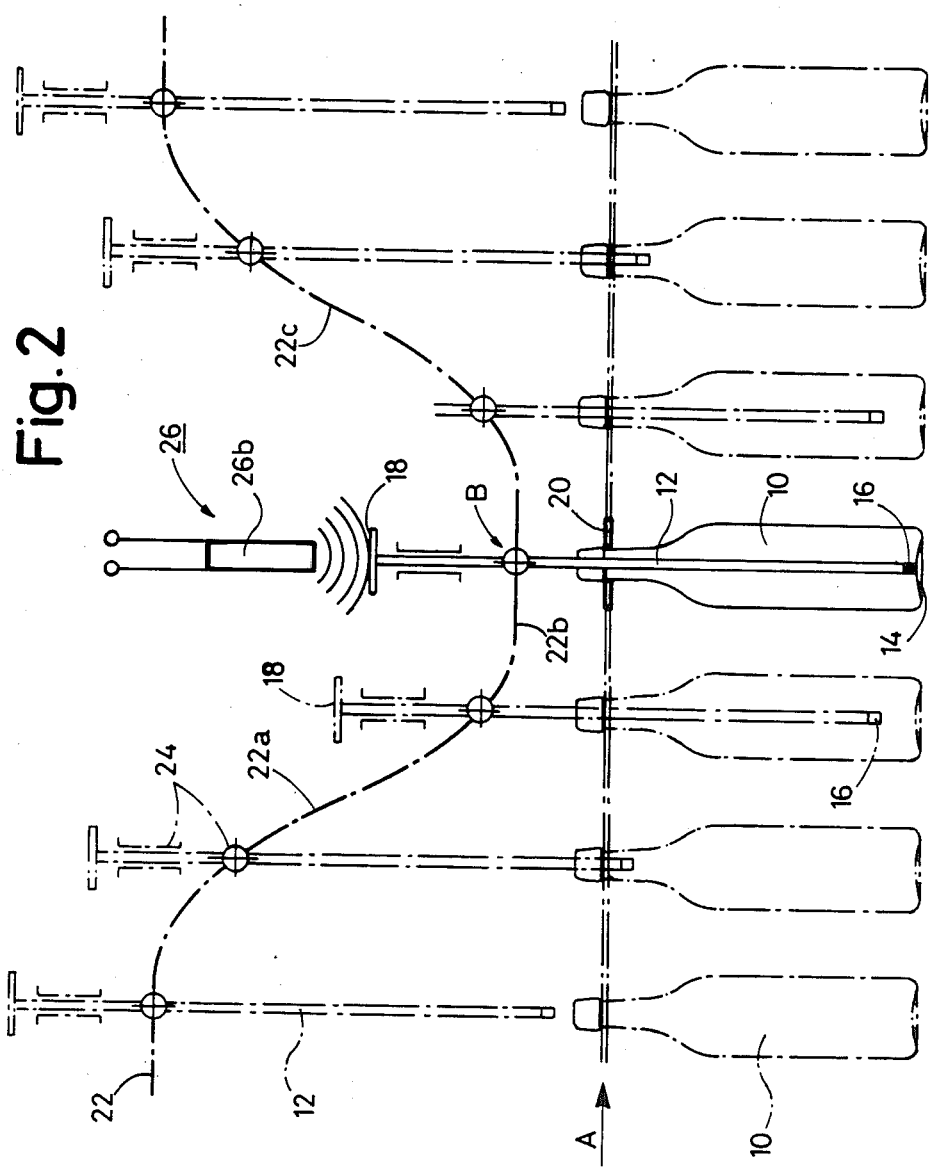

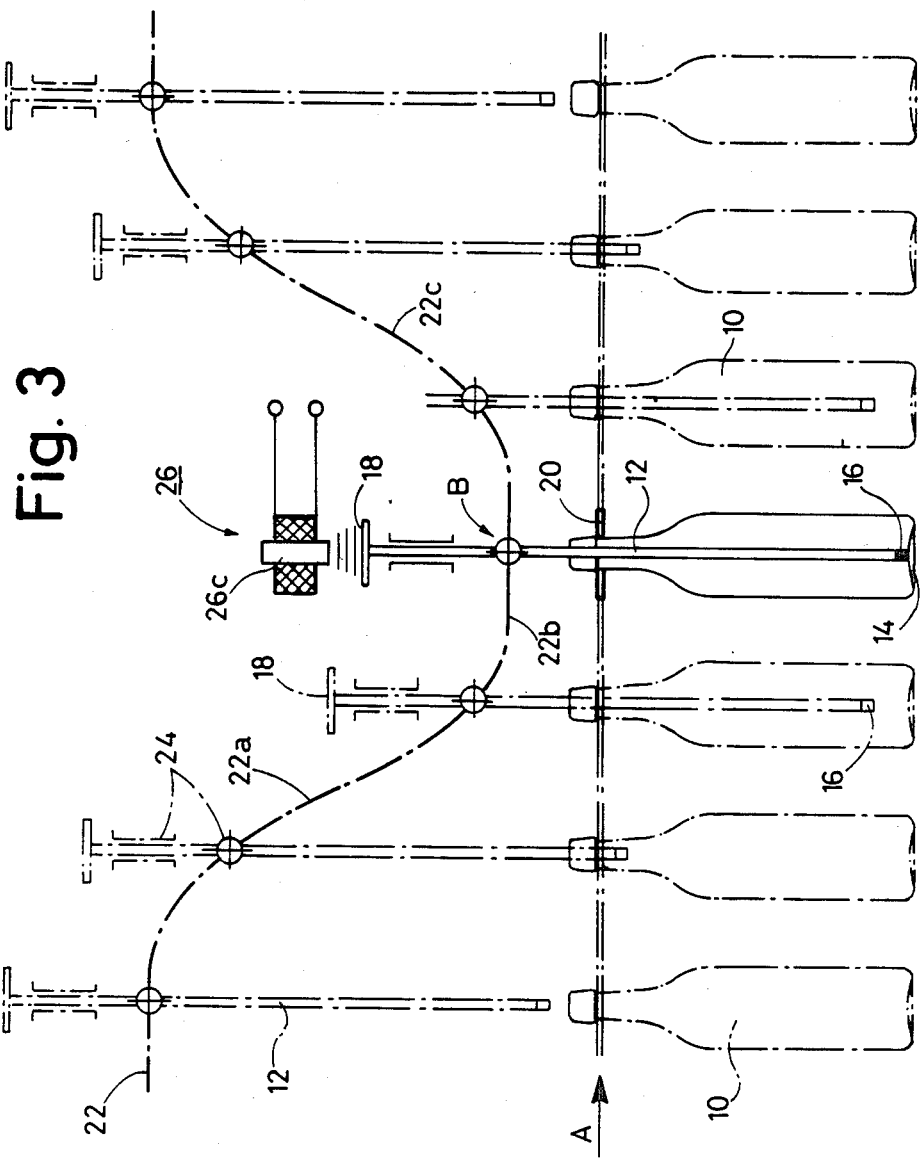

METHOD AND APPARATUS FOR THE STRESS TESTING OF GLASS CONTAINERS ARRANGED HANGING

The invention relates to a method for the stress testing of glass containers, which are arranged hanging, by impulse action on the bottom of the container by means of an impacting rod. In addition, the invention relates to an apparatus for carrying out the method, having a suspension appliance for grasping the glass container near its mouth and having a device for introducing and extracting the impacting rod.

Because of the amorphous structure of the glass, because of occlusions, because of their handling during manufacture, etc. glass containers are never free from internal stresses. During filling or refilling, the glass containers are exposed to external forces which can lead to the release of these stresses and hence to breakage. Since the breakage of containers at the bottler's is particularly unwelcome, glass containers are usually subjected to a stress test, that is to say a so-called stress inspection, while still in the glassworks or, in the case of the refilling of containers which have already been used one or more times, before the refilling.

Glass containers which are produced in the glassworks as mass-produced articles by the press-and-blow process or by the blow-and-blow process from new glass material or from remelted salvaged broken glass are not free from internal stresses because inevitably there are unequal wall thicknesses and, particularly in the case of production from salvaged broken glass, because occlusions are present. Cooling also inevitably leads to stresses. Stress pockets form in the glass container and do not become released immediately but only in the event of shock or under the loading during filling can lead to breakage. Hairline cracks in the glass can have the same effect. It is true that crak detectors are used in the glassworks in order to detect such hairline cracks but not all cracks can be detected because the detectors are only applied where cracks usually occur, for example at the neck of the glass container.

When salvaged broken glass is used for the production of glass containers, it frequently happens that the containers comprise ceramic occlusions and other possible residual particles which have been included in the melt. Stress pockets form particularly frequently round such occlusions or "stones" and may cause the breakage of the container if this is exposed to shock, for example during filling.

Returnable glass containers cause problems with regard to the risk of breakage because when, after manufacture in the glassworks, they have withstood the stress test carried out there, they are filled only once and then come into the glassworks as salvaged glass in order to be remelted. It is different with re-usable glass containers which may be refilled up to twenty times on the average. Even if such glass containers have withstood the first stress test in the glassworks and have also survived refilling one or more times, the residual stresses still contained in them may lead to breakage at any time. It is clear that this breakage causes many fewer problems at the glass manufacturer's than at the bottler's. Glass moulding machines work at production speeds of 300 to 400 glass containers per hour. Up to 3 percent of the containers break during the stress test following on their manufacture and are simply remelted, gives no problem in practice. On the other hand, bottlers work at production rates 60,000 to 70,000 filled glass containers per hour. It is obvious that in this case even a glass breakage rate of 1 or 0.5 per thousand leads to a considerable loss of production because when the glass breaks the contents of the glass container soil the filling machine and make extensive cleaning work necessary. It is even more of a problem if the glass breakage occurs only after filling, for example when the filled glass containers are already packed to a considerable height on a pallet and a filled glass container in the top tier on the pallet breaks.

It is therefore advisable to subject re-usuable glass containers to a stress test at the bottler's before each fresh filling operation in order to eliminate the problems outlined if possible.

For the said stress test, stress test machines are used in the glassworks (behind the glass moulding machine and the filling machine). In such a stess test machine a test turntable is provided into which the glass containers coming from a conveyor belt run in succession and are each gripped at the neck by tongs. The glass containers hanging freely in the tongs travel through the test turntable in a horizontal plane.

Arranged parallel to the path of the glass containers, in the test turntable, is a curved track on which carriages run, a carriage being associated with each pair of tongs. Each carriage carries an impacting rod which is arranged vertically and the lower end of which is directed towards the centre of the mouth of the glass container. On their way over the curved track, the carriages move the impacting rods into the glass containers and when the lower end of the impacting rod has reached a specific height above the bottom of the container, a trip gear is actuated. The released impacting rod then falls freely onto the bottom of the container and acts on this with an impact momentum depending on the height of fall and the weight of the impacting rod. The impacting rods are subsequently grasped against by a device provided on each carriage for the introduction and extraction of the impacting rods and are lifted out of the glass containers when the carriage again moves upwards on the curved track so that the glass containers can leave the test turntable again without hindrance. The weight of the impacting rod and the height of fall are variable so that different forces result for different glass containers (thin-walled or thick-walled, narrow-necked or wide-necked etc.), with which suitable test loads can be generated. An improvement in quality can be achieved by adjusting these parameters in the sense that fewer breakages occur later at the bottler's or, if the bottler is using the test machine, no breakages occur during the following filling.

The testing with the impacting rod falling on the bottom of the container is based on the idea of causing vibrations in the container which release its residual stresses so that glass breakage does or does not occur. With this impact testing, therefore, quasi conditions or shocks are simulated such as occur during the filling and transport of the glass container. Thus, during this stress test, the sum of the residual stresses present in the glass container as a result of hairline cracks, occlusions, unequal cooling of the glass container as a result of unequal wall thickness (the neck is usually considerably thinner than the bottom of the container), is either released and leads to the breakage of the container or is not released and the glass container remains whole, in which latter case it is assumed that it will then also withstand the stressing during filling or refilling and during transport.

This known stress test needs improvement in various ways. In the first place, the possibilities for variation with regard to the weight of the impacting rod (an impacting-rod weight of 0.5 to 1 kp is usual for example) and the height of fall (a height of fall of 80 to 100 mm is usual for example) are too little. A corresponding number of different weights of impacting rod cannot be provided for a 100 different glass containers to be tested. The height of fall cannot be varied to any desired extent either because there is only a limited amount of time and space in the test turntable in which the impacting rod can be released. Secondly, the selection of height of fall and weight of impacting rod is effected empirically and involves a great expenditure of time during the setting up of the test machine for each new type of glass container. If weight of impacting rod and/or height of fall are set too low, the risk of a glass breakage occurring later during filling is increased. If they are set too high an excessively large number of breakage may occur already during the stress test and the necks may also be pulled off the glass containers arranged hanging freely in the tongs. What is an even greater disadvantage is that if the weight of the impacting rod is too great and/or the height of fall is too great, it may also happen that no breakage occurs but additional stresses are built up, unnoticed, in the glass containers by the stress test and actually further increase the risk of breakage during the filling. Thirdly, glass moulding machines today work at a production rate of about 300 to 400 glass containers per minute whereas stress test machines of the type built by the inventor only reach throughputs of 100 to 120 glass containers per minute. This problem cannot be overcome in the existing stress test machines because, as mentioned, only a limited amount of space and time is available for allowing the impacting rod to fall and the test turntables cannot be made of any desired size both for reasons of space and for reasons of cost (each additional pair of tongs in the turntable means considerable additional investment costs).

It is the object of the invention to improve a method for the stress testing of glass containers which are arranged hanging, by impulse action on the on the bottom of the container by means of an impacting rod so that the impulse action can be varied in a simple manner without additional space and time requirements and the throughput of glass containers to be tested can be adapted to the production rate of existing glass moulding machines; in addition, an apparatus for carrying out the method is to be provided.

According to the invention, this problem is solved in that the impacting rod is set down on the bottom of the container and then the impulse action is effected by adjustable action of force on the impacting rod resting on the bottom of the container.

The apparatus for carrying out this method is characterised, according to the invention, by a device for placing the impacting rod on the bottom of the container and by a source of energy, which is adjustable in its action and which is disposed in the region of the end of the impacting rod remote from the bottom of the container.

Advantageous developments of the invention form the subject of the sub-claims.

With the method according to the invention, the restriction in space and time existing in conventional stress tests for the impulse action as a result of the parameters weight of impacting rod and height of fall which are only variable to a limited extent, is eliminated because the impulse action is effected according to the invention only after the impacting rod has already been placed on the bottom of the container. In a test turntable, the setting down can be effected long before the moment of the impulse action so that sufficient space and time are available for the impulse action itself for the impacting rod to be exposed to a plurality of impulse actions if necessary. Since, according to the invention, the impacting rod is already resting on the bottom of the container when it is exposed to the impulse action, there are numerous possibilites for producing the impulses, some of which are claimed in the sub-claims. According to the invention, the impulse amplitude and/or the impulse frequency can be varied as desired by mechanical, electrical or similar means, in order to be able to act on the glass container with an impulse approaching the optimum as far as possible. In the conventional stress test, only a decaying vibration can be produced in the glass container by a single fall of the impacting rod onto the bottom of the container, whereas by the method according to the invention, the form and the duration of the vibration produced in the container by the impulse action can be varied as desired in order to come as close as possible to the optimum for the stress test. Whereas in the conventional stress test, only a single blow can be produced as a result of a preset height of fall, according to the invention, the impulse action is so variable that rebound heights between impacting rod and container bottom can be produced which produce very fine vibrations in the glass container. In addition, as mentioned, sufficient space and time are available to repeat the impulse action as often as desired, if necessary. Furthermore, as a result of the method according to the invention, the throughput of glass containers during the stress test can easily be increased to values which correspond to the production rate of a glass moulding machine so that important advantages are achieved in time, space and costs.

The apparatus for carrying out the method according to the invention differs from conventional apparatuses of this type essentially in that a device is provided for setting down the impacting rod on the bottom of the container (instead of allowing it to fall on the bottom of the container) and that an adjustable source of energy, which may be any adjustable impulse generator, is disposed in the region of the end of the impacting rod resting on the bottom of the container which is remote from the bottom of the container.

In the development of the invention according to claim 2, the action of force is adjustable infinitely variably which, in the case of a magnetic or electromagnetic source of energy, can be effected by means of a potentiometer.

In the development of the invention according to claims 3 and 9, blows can be exerted on the end of the impacting rod resting on the bottom of the container which is remote from the bottom of the container, preferably by means of a rotatable eccentric with adjustable eccentricity.

In the development of the invention according to claims 4 and 10, the impulse action is effected by ultrasonic action, that is to say preferably by means of an ultrasonic transmitter. In this case, the glass containers move continuously past the ultrasonic transmitter which exposes the impacting rod resting on the bottom of the container to ultrasonic waves one or more times. As a result, the impacting rods are set impulsively in ultrasonic vibration which they transmit to the bottom of the container and through this to the whole of the container.

In the development of the invention according to claims 5 and 11, the source of energy may be magnetic actuating drive which acts on the impacting rod by magnetic force. It may simply be a question of using a magnet coil with a fixed core which lifts the impacting rod by a minimum height and then drives it down again, or of an actuating drive wherein an armature acts mechanically directly on the upper end of the impacting rod.

In the development of the invention according to claims 6 and 12, the impulse action of the impacting rod is again effected purely mechanically by means of a rocker, for example, which acts directly on the end of the impacting rod remote from the bottom of the container and is set in vibration by a similar device as in a vibratory table.

In the development of the invention according to claims 7, 13 and 14, impacting rods of small mass are used, that is to say preferably in the form of a hollow cylinder or of reinforced plastics material. Such an impacting rod of small mass can be set in high-frequency vibration as a result of which heavy and strong blows can be avoided in a simple manner. It must also be considerably more favourable to produce high-frequency vibrations in the container with a small mass instead of low-frequency ones with a large mass as in the conventional stress test method.

Several examples of embodiment of the invention are described in more detail below with reference to the drawings.

FIG. 1 shows one form of embodiment of the apparatus for carrying out the method according to the invention, with a rotatable eccentric, FIG. 2 shows a further form of embodiment of the apparatus with an ultrasonic transmitter and FIG. 3 shows yet another form of embodiment of the apparatus with a magnetic actuating drive.

FIG. 1 shows that part of a form of embodiment of an apparatus for the stress testing of glass containers 10 arranged hanging which is essential for the invention. The apparatus illustrated can be interpreted as part of the test turntable of a stress test machine, drawn as a planar development, but which have been modified, according to the invention in the sense that its impacting rods 12 are no longer suddenly released and allowed to fall onto the bottom 14 of the containers but instead are placed gently on the bottoms 14 of the containers by their lower end 16 and then exposed to an adjustable action of force at their upper end 18.

The glass containers 10 run into the apparatus in the direction of the arrow A from a conveyor (not illustrated) and are received in the apparatus, hanging at their necks, from tongs 20. Disposed adjacent to the path of the tongs 20 is curved track 22 on which carriages 24 are disposed, travelling at fixed distances apart corresponding to the mutual fixed distance from centre to centre of the glass containers 10 hanging in the tongs 20. The carriages 24, which moves over the curved track 22 towards the right in FIG. 1, move down over a descending portion 22a of the curved track 22, during which the impacting rods 12 are introduced into the mouths of the glass containers and their lower ends 16 are brought closer to the bottoms 14 of the containers.

When a carriage 24 reaches a horizontal portion 22b of the cuved track 22, it sets the impacting rod 12 down on the bottom 14 of the containers. The action of force through the upper ends 18 of the impacting rods is possible over the whole range of the horizontal portion 22b of the curved track 22. Following on the horizontal portion 22b of the curved track 22, the carriages 24 again move upwards over a rising portion 22c of the curved track and in the course of this pull the impacting rods out of the glass containers 10. In the centre of the horizontal portion 22b designated by B, a source of energy 26, which is adjustable in its action, is associated with the upper end 18 of the impacting rods 12. In the example of embodiment shown in FIG. 1, the source of energy comprises an eccentric 26a, in the example of embodiment shown in FIG. 2, an ultrasonic transmitter 26b, and in the example of embodiment shown in FIG. 3, a magnetic actuating drive 26c, which are described in detail below.

In the example of embodiment shown in FIG. 1, associated with the eccentric 26a is a flexible arm 26a' which is gripped at the right-hand end and, at the left-hand end, carries a ball 26a'' which strikes once on the upper end 18 of the impacting rod 12 during each revolution of the eccentric 21a. In all the examples of embodiment illustrated here, the upper end 18 of the rod 12 is constructed in the form of a plate but this only represents a preferred and not a necessary form of embodiment of this end. The action of force on the impacting rod 12 can be adjusted in a continuously variable manner by means of the speed of rotation of the eccentric 26a and/or the eccentricity. The form of embodiment of the eccentric 26a also serves only for illustration since instead of it, a cam plate could also be used which acts directly on the upper end 18 of the impacting rod 12. In the example of embodiment shown in FIG. 1, the rod 12 can be constructed in the form of a hollow cylinder which is provided at its lower end 16 with a pressure member, for example of plastics material. Alternatively, the rod 12 may simply be a bar of reinforced plastics material. In any case, the impacting rod can have a considerably smaller mass in comparison with the impacting rod used in the known stress test machine because instead of the acceleration of the rod due to gravity conventionally used to produce the blow, according to the invention the rod 12 resting on the bottom 14 of the container is merely acted upon impulsewise. If different glass containers 10 are to be tested, the rods 12 do not need to be altered but only the action of force on them.

The example of embodiment shown in FIG. 2 differs from the example of embodiment shown in FIG. 1 only in that the source of energy 26 comprises ultrasonic transmitter 26b instead of the eccentric. All statements made about the example of embodiment in FIG. 1 therefore apply accordingly to the example of the embodiment shown in FIG. 2. The ultrasonic transmitter 26b sets the impacting rods 12 in ultrasonic vibration which these transmit to the bottom 14 of the container. The transmitter may be a conventional piezoelectric oscillator crystal, the amplitute and/or frequency of oscillation of which are adjustable in the usual manner.

In the example of embodiment shown in FIG. 3, the source of energy 26 comprises a magnetic actuating drive 26c. This is represented as a magnet coil with a fixed core which, at the frequency of the exciting voltage of the magnet, attracts and repels the plate, which is provided at the upper end 18 of the rod and consists of iron or the like. The impulse length can be adjusted in a simple manner by the duration of the application of the exciting voltage. Apart from the plate, the whole of the rest of the impacting rod 12 could also consist of iron or the like. An armature of the magnetic actuating drive could also be placed on the plate at the upper end 18 and be adapted for axial movement (not illustrated), in which case the oscillating movement of the armature would then be transmitted directly to the impacting rod 12. In this case, of course, the plate and/or the rod would not need to consist of iron or the like but could also consist of reinforced plastics material as in the previous two examples of embodiment.

In all three examples of embodiment illustrated, the horizontal portion 22b of the cuved track 22 can be made any length and the source of energy 26 can be conveyed with the impacting rod 12 resting on the bottom 14 of the container over a portion of the travel so that any desired amount of time is available for the repeated action of force on the rod.

Instead of the three different sources of energy illustrated in FIGS. 1 to 3, a rocker (not illustrated) could also be used which, at one end, acts directly on the plate of the impacting rod 12 resting on the bottom 14 of the container and, at the other end, is set in vibration by a drive device as in a vibratory table. In this case, the impulse length of the action of force could be adjusted by the length of rocker in the region of contact with the plate or by the duration of vibration of the rocker.

I claim:

1. A method for the stress testing of glass containers, which are arranged hanging, by impulse action on the bottom of the container by means of an impacting rod, characterised in that the impacting rod is placed down on the bottom of the container and then the impulse action is effected by an adjustable action of force on the impacting rod resting on the bottom of the container.

2. A method as claimed in claim 1, characterised in that the action of force is adjusted in a continuously variable manner in magnitude and/or duration.

3. A method as claimed in claim 1, characterised in that the action of force is produced by one or more blows on the end of the impacting rod remote from the bottom of the container.

4. A method as claimed in claim 1, characterised in that the action of force is produced by ultrasonic action on the end of the impacting rod remote from the bottom of the container.

5. A method as claimed in claim 1, characterised in that the action of force is produced by the action of magnetic force on the end of the impacting rod remote from the bottom of the container.

6. A method as claimed in claim 1, characterised in that the action of force is produced by mechanical vibrations, produced as in the case of a vibrating table and acting directly on the end of the impacting rod remote from the bottom of the container.

7. A method as claimed in claim 1, characterised in that an impacting rod of small mass is used.

8. An apparatus for performing stress testing of glass containers having an interior cavity with a bottom, said apparatus comprising:
   grasping means for grasping a glass container near its mouth and holding the container in a suspended condition;
   means for introducing and extracting through the container mouth a first end of an impacting rod, said rod position to be adjacent to the container bottom; and
   adjustable energy source means associated with an opposite second end of the impacting rod for transmitting energy to the glass container.

9. An apparatus as claimed in claim 8, characterized in that the adjustable energy source means comprises a rotatable eccentric (26a) with adjustable eccentricity, acting on the end (18) of the impacting rod (12) remote from the bottom (14) of the container.

10. An apparatus as claimed in claim 8, characterized in that the adjustable energy source means (26) comprises an ultrasonic transmitter (26b).

11. An apparatus as claimed in claim 8, characterized in that the adjustable energy source means (26) comprises a magnetic actuating drive (26c).

12. An apparatus as claimed in claim 8, characterized in that the adjustable energy source means (26) is a device constructed on the vibrating table principle.

13. An apparatus as claimed in claim 8, characterized in that the impacting rod (12) is a hollow cylinder which is provided with a pressure member at its end (16) adjacent to the bottom (14) of the container.

14. An apparatus as claimed in claim 8, characterized in that the impacting rod (12) consists at least partially of reinforced plastics material.

* * * * *